(12) United States Patent
Yoshida et al.

(10) Patent No.: US 9,404,601 B2
(45) Date of Patent: Aug. 2, 2016

(54) SOLENOID VALVE

(71) Applicant: SMC CORPORATION, Chiyoda-ku (JP)

(72) Inventors: Masami Yoshida, Ryugasaki (JP); Hideaki Yashiro, Moriya (JP); Takashi Hirano, Moriya (JP)

(73) Assignee: SMC CORPORATION, Chiyoda-ku (JP)

( * ) Notice: Subject to any disclaimer, the term of this patent is extended or adjusted under 35 U.S.C. 154(b) by 0 days.

(21) Appl. No.: 14/604,055

(22) Filed: Jan. 23, 2015

(65) Prior Publication Data

US 2015/0240964 A1 Aug. 27, 2015

(30) Foreign Application Priority Data

Feb. 21, 2014 (JP) ................. 2014-031538

(51) Int. Cl.
*F16K 31/06* (2006.01)
*A61M 16/20* (2006.01)
*A62B 9/02* (2006.01)

(52) U.S. Cl.
CPC ............ *F16K 31/0655* (2013.01); *A61M 16/20* (2013.01); *F16K 31/0679* (2013.01); *A62B 9/02* (2013.01)

(58) Field of Classification Search
CPC . F16K 31/06; F16K 31/0603; F16K 31/0624; F16K 31/0641; F16K 31/0655; F16K 31/0672; A61M 16/20; A62B 9/02; B01D 53/04
USPC ................. 251/129.15, 129.17, 117
See application file for complete search history.

(56) References Cited

U.S. PATENT DOCUMENTS

| | | | | |
|---|---|---|---|---|
| 5,333,643 | A | * 8/1994 | Gilchrist | ............. F16K 31/0658 137/605 |
| 5,406,975 | A | * 4/1995 | Nakamichi | ......... F16K 31/0655 137/495 |
| 5,419,367 | A | * 5/1995 | Noya | ................. F02M 25/0836 137/495 |
| 2011/0000563 | A1 | * 1/2011 | Ito | ..................... F02M 25/0836 137/596.17 |

FOREIGN PATENT DOCUMENTS

| | | |
|---|---|---|
| JP | 52-155229 | 11/1977 |
| JP | 2001 90860 | 4/2001 |
| KR | 10-2010-0122585 A | 11/2010 |
| KR | 10-2013-0048232 A | 5/2013 |

OTHER PUBLICATIONS

Office Action issued Dec. 1, 2015 in Korean Patent Application No. 10-2015-0023403 (with Partial English translation).

* cited by examiner

*Primary Examiner* — William McCalister
*Assistant Examiner* — Ian Paquette
(74) *Attorney, Agent, or Firm* — Oblon, McClelland, Maier & Neustadt, L.L.P (57) ABSTRACT

A solenoid valve is arranged in a flow path in which a fluid flows in both directions, and is constituted from a solenoid valve mounting portion, in which a first port and a second port are formed, and a single solenoid valve portion. A first flow rate stabilizing orifice is disposed between the first port and a valve body of the solenoid valve portion, and a second flow rate stabilizing orifice is disposed between the second port and the valve body. A bypass orifice is disposed in a bypass flow path that bypasses the first flow rate stabilizing orifice and the second flow rate stabilizing orifice.

7 Claims, 4 Drawing Sheets

SOLENOID VALVE

CROSS-REFERENCE TO RELATED APPLICATION

This application is based upon and claims the benefit of priority from Japanese Patent Application No. 2014-031538 filed on Feb. 21, 2014, the contents of which are incorporated herein by reference.

BACKGROUND OF THE INVENTION

1. Field of the Invention

The present invention relates to a solenoid valve in which a fluid flows at substantially the same flow rate in both directions of a flow path.

2. Description of the Related Art

Heretofore, an oxygen generating apparatus for medical use has been known in which two adsorption columns are provided which adsorb nitrogen from compressed air in order to generate concentrated oxygen. With this type of oxygen generating apparatus, using the two adsorption columns alternately, so that concentrated oxygen can be generated from the compressed air continually over an extended period of time, during the time that nitrogen is being adsorbed by one of the adsorption columns, nitrogen is removed from the other of the adsorption columns to enable regeneration of the other adsorption column. In this manner, when the two adsorption columns are switched and used alternately, a pressure equalizing valve is provided so that the pressures of the flow paths that are connected to the adsorption columns can be equalized rapidly. Moreover, during the time that the other of the adsorption columns is regenerating while nitrogen is being adsorbed by the one adsorption column, a portion of the concentrated oxygen that is generated in the one adsorption column is supplied to the other of the adsorption columns through an orifice that is formed in a passage that bypasses the pressure equalizing valve.

In addition, as the structure of the pressure equalizing valve, a symmetrical configuration is sometimes adopted, in which two solenoid valves of the same structure are disposed in a manifold block. Thus, in the case that the adsorption column that is used for generating concentrated oxygen is switched from one to the other, or is switched from the other to the one, while taking into consideration the fact that the direction of flow of the fluid is reversed, a constant flow rate is ensured in either of these cases.

However, as stated above, in the manifold type pressure equalizing valve, which is equipped with two solenoid valves, an increase in the size of the apparatus cannot be avoided. Further, the flow passages formed in the manifold block are complex, and as a result, a problem is noted in that the oxygen generating apparatus as a whole is unavoidably expensive.

Thus, for example, a pressure equalizing valve for an oxygen generating apparatus has been proposed, as disclosed in Japanese Laid-Open Patent Publication No. 2001-090860. In the pressure equalizing valve, for addressing a problem that occurs in the case that one solenoid valve is provided, or more specifically, in which the flow rate differs depending on the direction in which the fluid flows, in the event that the valve is opened in opposition to a high pressure, a current when the valve body is attracted is set based on the measurement of a current and an energizing time necessary for such a fluid pressure, whereby the attraction force of the valve body is increased, and after attraction of the valve body, a predetermined current is made to flow, which is as small as possible needed to maintain the attracted state. Consequently, even if a small size solenoid valve is used, a large current is made to flow and a large attraction force can be obtained only during attraction of the valve body, and in the case that a fluid flows in both directions with respect to the single solenoid valve, opening and closing of the valve can be controlled so that, in either of such directions, the flow rate is kept constant without being affected by the fluid pressure.

SUMMARY OF THE INVENTION

With the aforementioned pressure equalizing valve of Japanese Laid-Open Patent Publication No. 2001-090860, although only one solenoid valve is required, a specialized control circuit is needed for controlling opening and closing of the solenoid valve, so that a large current is made to flow for attracting the valve body and a small current is made to flow for maintaining the attracted state, leading to a disadvantage in that equipment costs are increased and the control operations are complex.

The present invention has been devised taking into consideration the aforementioned problems, and has the object of providing a solenoid valve, which is operated by simple controls, and further in which, while a structure equipped with a single solenoid valve portion is provided, a difference in flow rate due to the direction in which the fluid flows does not occur, and there is no need for a specialized control circuit for controlling the currents used to attract the valve body and maintain the attracted state.

A solenoid valve according to the present invention is arranged in a flow path in which a fluid flows in both directions, and is constituted from a solenoid valve mounting portion, in which a first port and a second port are formed, and a single solenoid valve portion. A first flow rate stabilizing orifice is disposed between the first port and a valve body of the solenoid valve portion, and a second flow rate stabilizing orifice is disposed between the second port and the valve body of the solenoid valve portion. Further, a bypass orifice is disposed in a bypass flow path that bypasses the first flow rate stabilizing orifice and the second flow rate stabilizing orifice.

According to the above-described solenoid valve, in the event that fluid flows from the first port to the second port, or in the event that fluid flows from the second port to the first port, even if the flow direction of the fluid in the vicinity of the valve body is different, the flow rate is governed by the flow rate stabilizing orifices, in particular the downstream side flow rate stabilizing orifice from among the first flow rate stabilizing orifice and the second flow rate stabilizing orifice. For this reason, a structure can be provided in which a difference in flow rates does not occur, whether in the case that the fluid flows from the first port to the second port, or in the case that the fluid flows from the second port to the first port.

Further, by constituting the aforementioned solenoid valve from the solenoid valve mounting portion in which the first port and the second port are formed, and the single solenoid valve portion, a reduction in size of the solenoid valve can be realized without the need for a manifold structure. Furthermore, there is no need for a specialized control circuit for the purpose of controlling the solenoid valve portion.

In the above-described solenoid valve, a first passage that leads to the first flow rate stabilizing orifice, and a second passage that leads to the second flow rate stabilizing orifice may be formed in the solenoid valve mounting portion, and a valve seat on which the valve body can be seated may be formed in one open end of one of the first passage and the second passage. Furthermore, the one open end is circular shaped, and another open end of another one of the first passage and the second passage is annularly shaped surrounding a circumference of the one open end. Owing thereto, the structure for arranging the valve body with respect to the flow path can be simplified.

Further, the first port and the second port may be disposed on opposite ends of a bore that is formed in the solenoid valve mounting portion, the first flow rate stabilizing orifice and the second flow rate stabilizing orifice may be constituted from passages defined by one surface of a partition wall disposed in the bore and an inner wall surface of the bore, and the bypass flow path may be disposed on an opposite side of the partition wall from the one surface.

According to the structure described above, the first flow rate stabilizing orifice and the second flow rate stabilizing orifice can be constituted from passages defined by one surface of the partition wall disposed in the bore and an inner wall surface of the bore. Together therewith, the bypass flow path that bypasses the first flow rate stabilizing orifice and the second flow rate stabilizing orifice can be constituted on an opposite side of the partition wall from the one surface. Therefore, the first flow rate stabilizing orifice, the second flow rate stabilizing orifice, and the bypass orifice can be arranged compactly in the interior of the solenoid valve mounting portion, in which the first port and the second port are formed.

Furthermore, the bypass orifice may be disposed in a substantially central position in a longitudinal direction of the bypass flow path, and a cross sectional area of the bypass flow path may be substantially constant from respective ends in the longitudinal direction to predetermined positions in vicinity of the bypass orifice, and the cross sectional area may gradually become smaller from the predetermined positions toward the bypass orifice.

In accordance with the above-described structure, in the bypass flow path that includes the bypass orifice, the flow of the fluid can be made smoothly laminar.

Further, preferably, the solenoid valve mounting portion is formed from a resin. In this case, since the solenoid valve mounting portion including the partition wall is formed from a resin, it is unnecessary for the first flow rate stabilizing orifice, the second flow rate stabilizing orifice, and the bypass orifice to be formed from separate components or formed by a cutting process, and thus the solenoid valve mounting portion can be manufactured inexpensively at a low cost.

According to the solenoid valve of the present invention, a structure can be provided in which a difference in flow rate due to the direction of flow of a fluid does not occur. In addition, since there is no need for a manifold structure, the solenoid valve can be reduced in size, and furthermore, there is no need for a specialized control circuit.

The above and other objects, features and advantages of the present invention will become more apparent from the following description when taken in conjunction with the accompanying drawings, in which a preferred embodiment of the present invention is shown by way of illustrative example.

DESCRIPTION OF THE PREFERRED EMBODIMENTS

Below, a preferred embodiment of a solenoid valve according to the present invention will be described in detail with reference to the accompanying drawings.

Figure 1:
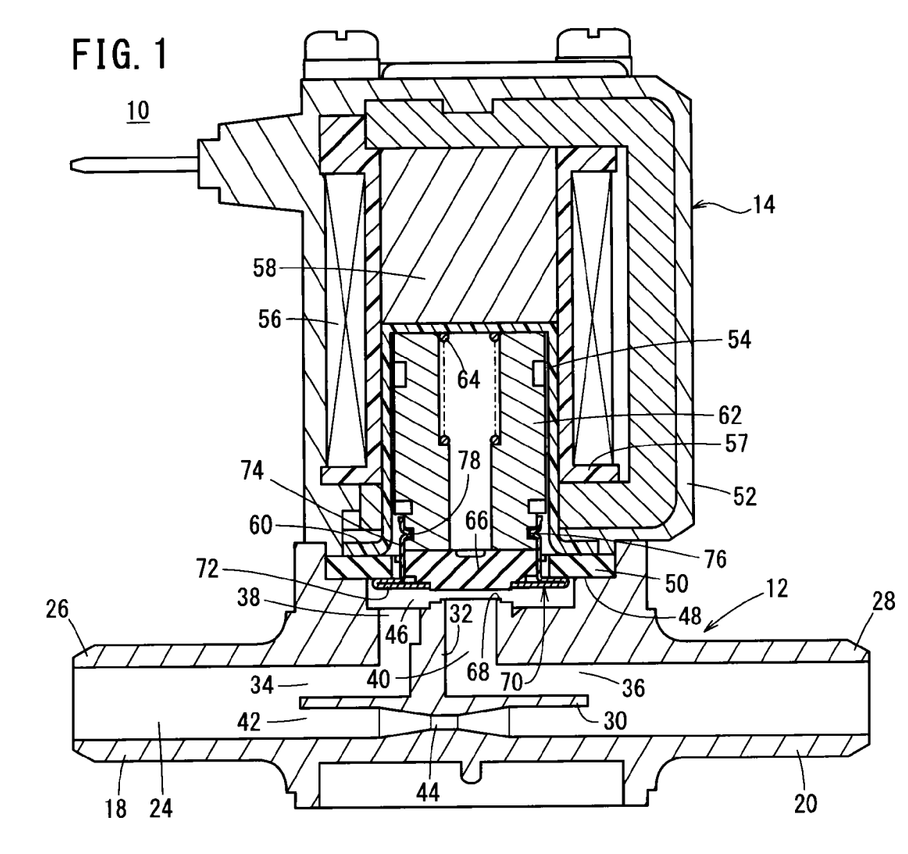
FIG. 1 is a vertical cross sectional view of a solenoid valve according to an embodiment of the present invention.
Figure 2:
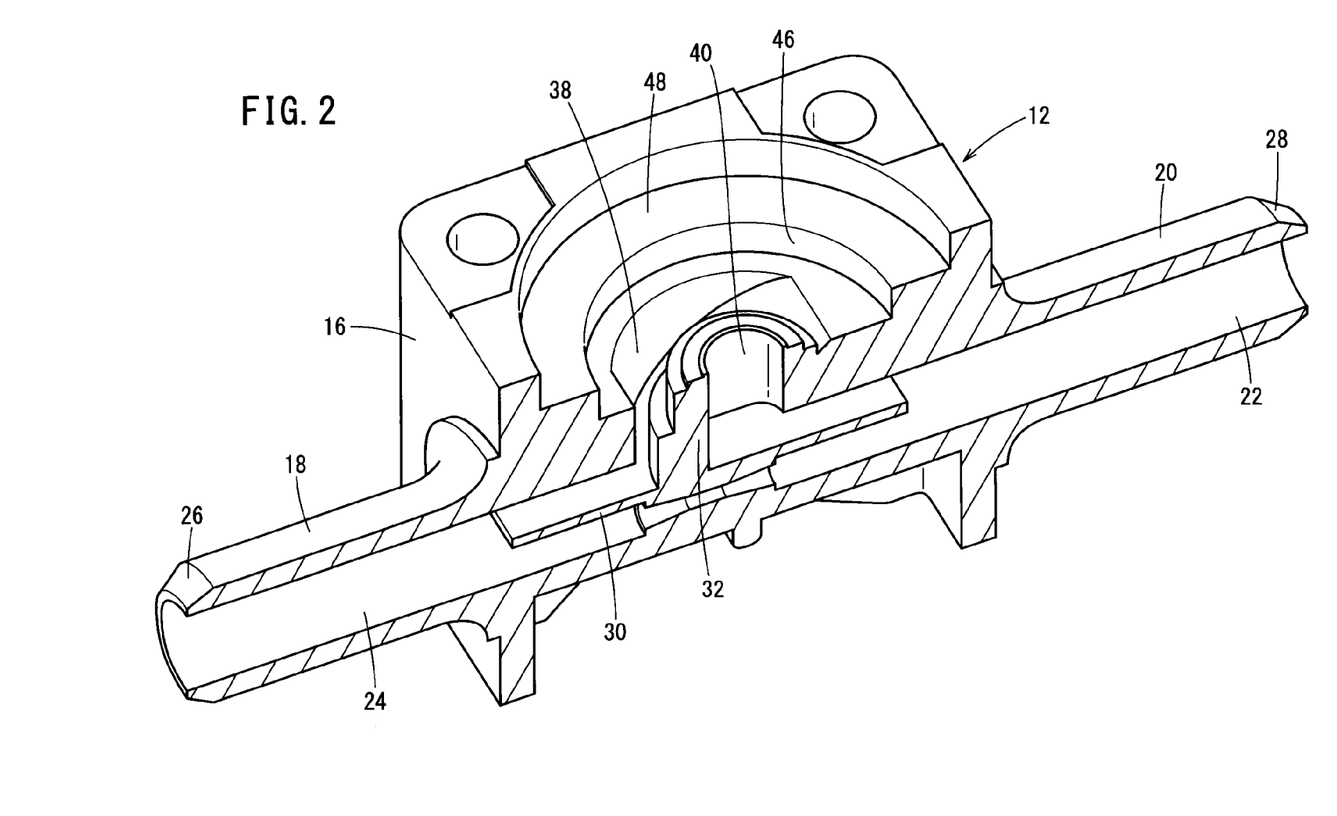
FIG. 2 is a perspective view in which a solenoid valve mounting portion that constitutes part of the solenoid valve shown in FIG. 1 is illustrated in cutaway form.

A solenoid valve 10 according to an embodiment of the present invention is shown in FIGS. 1 and 2, and for example, is used with a later-described oxygen concentrating device 80.

The solenoid valve 10 is constituted from a solenoid valve mounting portion 12 made of resin, and a single solenoid valve portion 14. As shown in FIG. 2, the solenoid valve mounting portion 12 includes a substantially rectangular parallelepiped shaped body 16, and a first tubular body 18 and a second tubular body 20 that extend outwardly from respective opposite side wall surfaces of the body 16. The solenoid valve mounting portion 12 includes a bore 22 that extends in an axial direction of the first tubular body 18 and the second tubular body 20, and a flow path 24 is formed in the interior of the first tubular body 18 and the second tubular body 20. Accordingly, open ends of the first tubular body 18 and the second tubular body 20 function respectively as a first port 26 and a second port 28.

Directly beneath the solenoid valve portion 14 of the flow path 24 that extends from the first port 26 to the second port 28, a first partition wall 30 is disposed that extends in the longitudinal direction of the flow path 24, and a second partition wall 32, which extends vertically, is erected with respect to the first partition wall 30 from a position substantially in the center in the longitudinal direction of the first partition wall 30. More specifically, a first flow rate stabilizing orifice 34 proximate the first port 26, and a second flow rate stabilizing orifice 36 proximate the second port 28 are formed respectively and substantially symmetrically, sandwiching the second partition wall 32 therebetween, and thereby dividing the flow path 24 into two parts on an upper side of the first partition wall 30, as shown in FIG. 1.

The second flow rate stabilizing orifice 36 is bent and rises upwardly from the second partition wall 32, and communicates with a later-described bottom space 46 as a second passage 40 that is circularly shaped in cross section. On the other hand, the first flow rate stabilizing orifice 34 is bent and rises upwardly from the second partition wall 32, expands in an annular shape while inclining in surrounding relation to an outer side of the second passage 40, and communicates with the bottom space 46 as a first passage 38. As shown in FIG. 1, due to the presence of a valve seat 68 for a later-described valve body 66, an open end of the second passage 40, which communicates with the bottom space 46, is disposed in a slightly more elevated position than an open end of the first passage 38.

On the lower side of the first partition wall 30 in FIG. 1, a bypass flow path 42 is formed that bypasses the first flow rate stabilizing orifice 34 and the second flow rate stabilizing orifice 36, and a bypass orifice 44 is disposed substantially in the center in the longitudinal direction of the bypass flow path 42. As can be understood from FIGS. 1 and 2, the bypass flow path 42 is defined by cylindrical regions that extend from both ends in the longitudinal direction of the first partition wall 30 up to predetermined positions proximate the bypass orifice 44. Further, at conical regions that extend from such predetermined positions up to the bypass orifice 44, conical spaces with a narrow flow path area are included. More specifically, the cross sectional area of the bypass flow path 42 is substantially constant from respective ends in the longitudinal direction of the bypass flow path 42 to predetermined positions in the vicinity of the bypass orifice 44, becomes gradually smaller from the predetermined positions toward the bypass orifice 44, and is smallest at the position of the bypass orifice 44.

As shown in FIGS. 1 and 2, in the body 16, an annular stepped portion 48 is formed from an annular space at the upper end leading to the bottom space 46 thereof. A seal member 50, which is formed with a large diameter hole in the center, is seated on the stepped portion 48.

The solenoid valve portion 14 includes a rectangular-shaped housing 52 and a cylindrical casing 54. In the interior of the housing 52, an electromagnetic coil 56, a bobbin 57, and a fixed iron core 58, etc., are accommodated. A lower end of the housing 52 is seated on an annularly shaped upper end of the body 16, and the housing 52 is fixed to the body 16 by a means such as non-illustrated bolts or the like. The cylindrical casing 54 is disposed on the inside of the bobbin 57 abutting against the fixed iron core 58, and a movable iron core 62, which is movable in an axial direction, is accommodated in the cylindrical casing 54. The cylindrical casing 54 is of a hat-like shape that opens only on the downward side, with a flange 60 being formed on the open end. When the housing 52 is fixed to the body 16, the seal member 50 is sandwiched between the flange 60 and the stepped portion 48 of the body 16. A coil spring 64 that biases the movable iron core 62 downwardly is disposed between the movable iron core 62 and a ceiling surface of the cylindrical casing 54.

As shown in FIG. 1, the valve body 66 is fixed to a lower end of the movable iron core 62. The valve body 66, which is of a thick disk-like shape, is made from an elastic material, and a circular shaped bulging portion, with a predetermined diameter to cover the valve seat 68 that is formed on the open end of the second passage 40, is formed on the lower surface of the valve body 66.

The valve body 66 is fixed to the movable iron core 62 through a fastener 70. The fastener 70 comprises an annular plate member 72 that surrounds the circular shaped bulging portion. The annular plate member 72 is bent inwardly to come into contact with a lower surface of the seal member 50, and then comprises a metallic annular body that extends upwardly as a leg portion 74. The upwardly rising leg portion 74 is inserted through a gap formed between a large diameter hole of the seal member 50 and an outer circumferential edge of the valve body 66, and terminates in the vicinity of a lower end of the movable iron core 62. In the vicinity of the lower end of the movable iron core 62, an encircling engagement groove 76 is formed. An engagement member 78, which projects inwardly from the leg portion 74, engages with the engagement groove 76.

The solenoid valve 10 according to the present embodiment is constructed basically as described above. Next, operations and advantages of the solenoid valve 10 will be explained.

When the fluid pressure of the first port 26 is greater than the fluid pressure of the second port 28, and the electromagnetic coil 56 is energized to drive the valve body 66 to an open position, the fluid flows from the first port 26 toward the second port 28. More specifically, the fluid that flows in from the first port 26 passes through the first flow rate stabilizing orifice 34 and is reduced in pressure, and thereafter, the fluid is introduced from the first passage 38 into the bottom space 46. The flow direction of the fluid changes in the vicinity of the valve seat 68, and the fluid flows through the second passage 40, which is positioned substantially in the center of the bottom space 46, further passes through the second flow rate stabilizing orifice 36, and then flows out from the second port 28. At this time, although turbulence is generated in the vicinity of the valve body 66 due to the change in flow direction, a throttling effect, which is produced by the second flow rate stabilizing orifice 36 that the fluid passes through thereafter, is large, and thus the flow rate of the fluid that flows from the first port 26 to the second port 28 is governed by the second flow rate stabilizing orifice 36.

On the other hand, when the fluid pressure of the second port 28 is greater than the fluid pressure of the first port 26, and the electromagnetic coil 56 is energized to drive the valve body 66 to an open position, the fluid flows from the second port 28 toward the first port 26. More specifically, the fluid that flows in from the second port 28 passes through the second flow rate stabilizing orifice 36 and is reduced in pressure, and thereafter, the fluid passes through the second passage 40 and is introduced into the bottom space 46 while colliding with the valve body 66 and spreading out circumferentially around the valve body 66. In addition, after passing through the first passage 38, the fluid passes through the first flow rate stabilizing orifice 34, and then flows out from the first port 26. At this time, although turbulence is generated in the vicinity of the valve body 66 due to colliding with the valve body 66, a throttling effect, which is produced by the first flow rate stabilizing orifice 34 that the fluid passes through thereafter, is large, and thus the flow rate of the fluid that flows from the second port 28 to the first port 26 is governed by the first flow rate stabilizing orifice 34.

In this manner, in the event that fluid flows from the first port 26 to the second port 28, or in the event that fluid flows from the second port 28 to the first port 26, even if the flow direction when the fluid passes in the vicinity of the valve body 66 is different, since the flow rate is governed by the first flow rate stabilizing orifice 34 or the second flow rate stabilizing orifice 36, which are formed symmetrically, a difference in flow rate does not occur.

Moreover, the fluid that faces the bottom space 46 passes through the gap formed between the large diameter hole of the seal member 50 and the outer circumferential edge of the valve body 66, and furthermore, exerts a pressure by flowing around an upper side of the movable iron core 62. In addition, in the case that the fluid flows from the first port 26 to the second port 28, the flow rate when the fluid enters into the second passage 40 from the bottom space 46 increases while the pressure of the fluid decreases. On the other hand, in the case that the fluid flows from the second port 28 to the first port 26, the flow rate when the fluid enters into the bottom space 46 from the second passage 40 decreases while the pressure of the fluid increases. For this reason, in the case that the fluid flows from the first port 26 to the second port 28, or in the case that the fluid flows from the second port 28 to the first port 26, the force applied to the movable iron core 62 is different, and the position of the valve body 66 changes. However, in either of such cases, since the first flow rate stabilizing orifice 34 or the second flow rate stabilizing orifice 36 is provided, which governs the flow rate on the downstream side, there is no need for a control circuit as was required in the conventional art.

Figure 3:
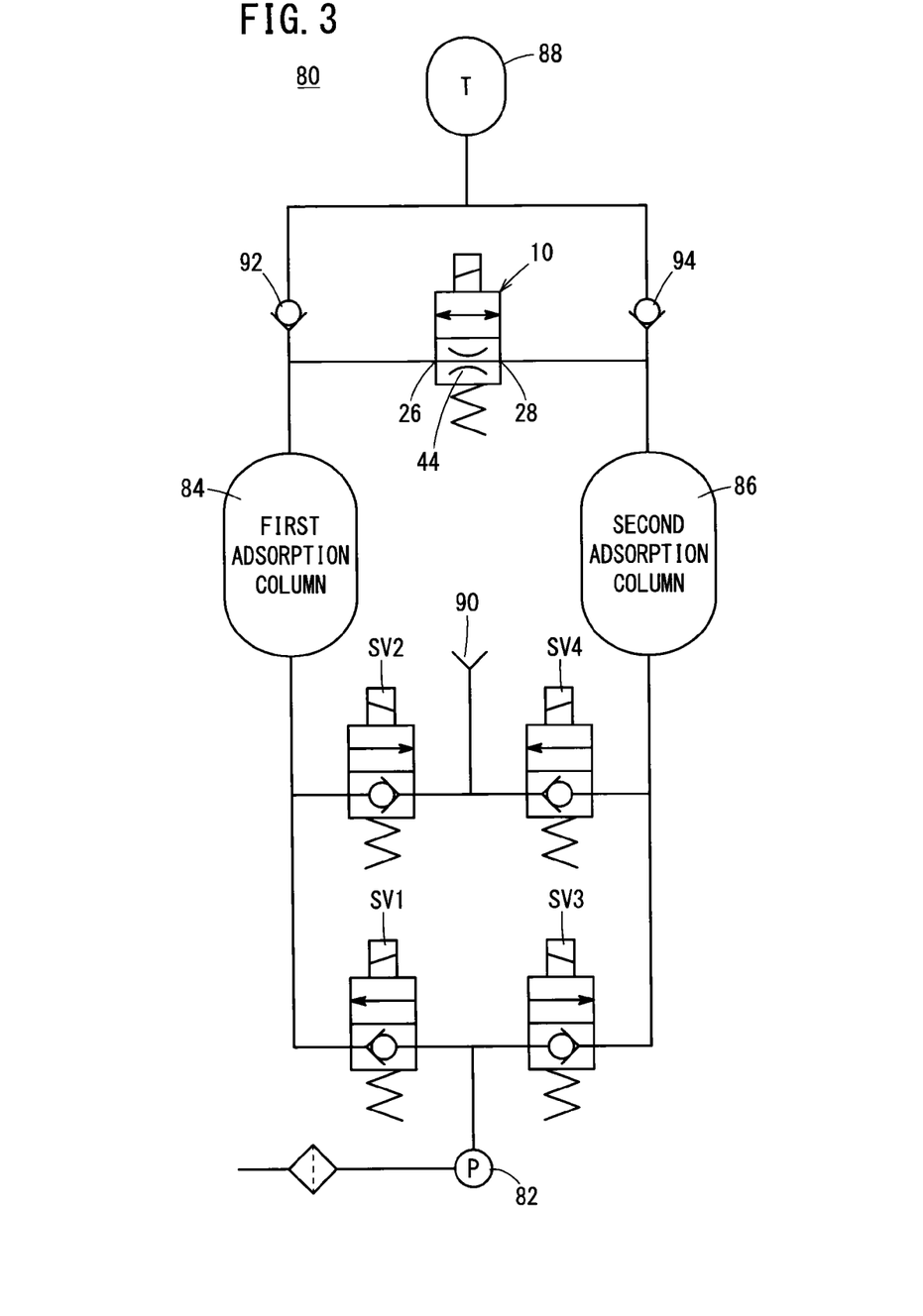
FIG. 3 is a fluid circuit diagram of an oxygen concentrating device in which the solenoid valve of the present invention is used.
Figure 4:
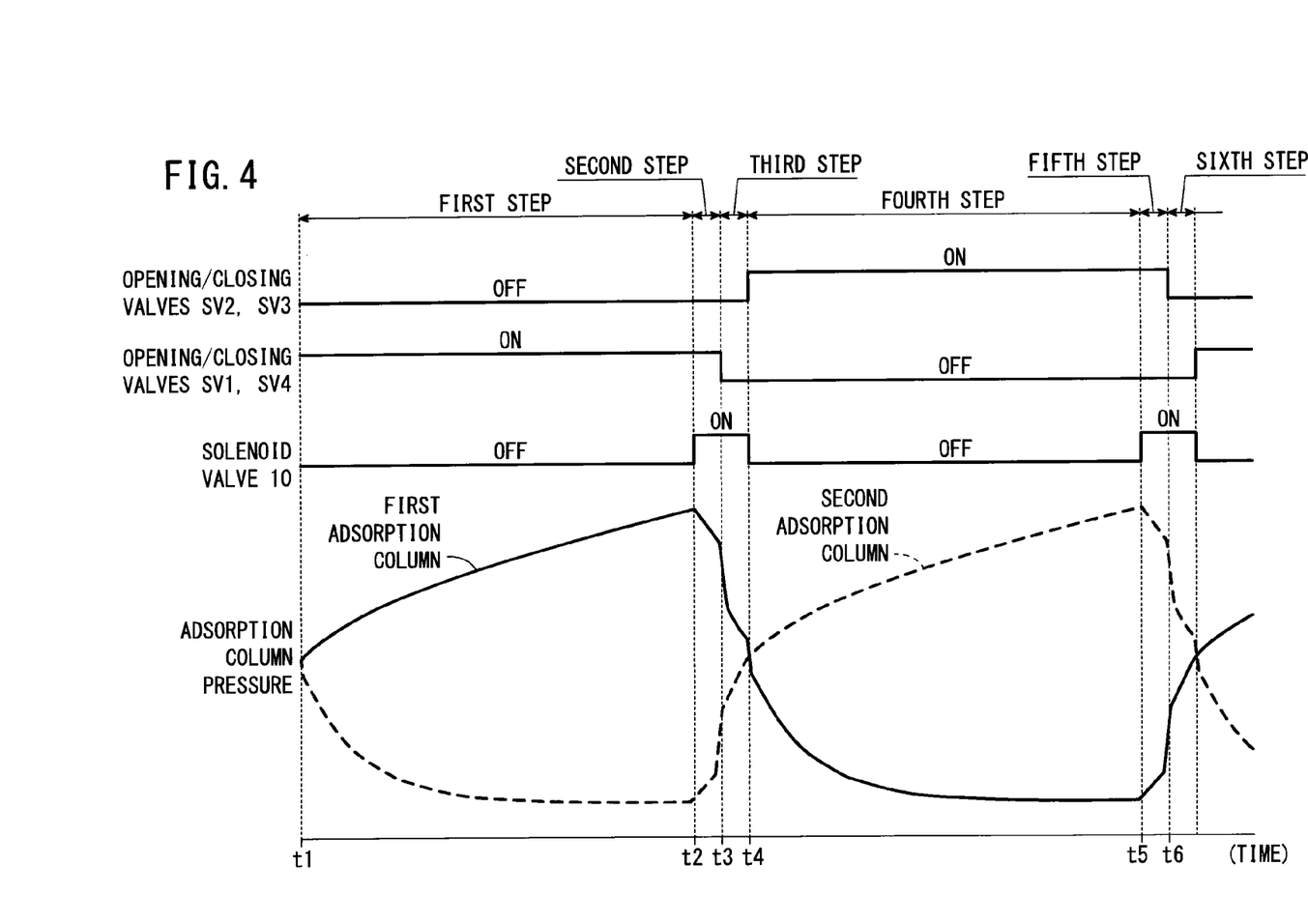
FIG. 4 is a timing chart for explaining operations of the oxygen concentrating device shown in FIG. 3.

An example in which the solenoid valve 10 according to the present embodiment is applied to the oxygen concentrating device 80 will be described below with reference to FIGS. 3 and 4.

The oxygen concentrating device 80 is equipped with a compressor 82, a first adsorption column 84, a second adsorption column 86, and a tank 88. The first adsorption column 84 and the second adsorption column 86 are used alternately, and nitrogen is adsorbed from compressed air that is produced by the compressor 82, thereby increasing the oxygen density, and the concentrated oxygen is stored in the tank 88. Zeolite, which serves as a nitrogen adsorbent, is incorporated into the first adsorption column 84 and the second adsorption column 86.

An opening/closing valve SV1 is disposed in a flow path connecting the compressor 82 and the first adsorption column 84, and another opening/closing valve SV2 is disposed in a flow path connecting the first adsorption column 84 and a discharge port 90. When the opening/closing valve SV1 is in an ON state (i.e., when energized), fluid can pass freely between the compressor 82 and the first adsorption column 84, and when the opening/closing valve SV1 is in an OFF state (i.e., when not energized), flow of the fluid from the compressor 82 to the first adsorption column 84 is shut off. When the opening/closing valve SV2 is in an ON state, fluid can pass freely between the first adsorption column 84 and the discharge port 90, and when the opening/closing valve SV2 is in an OFF state, flow of the fluid from the first adsorption column 84 to the discharge port 90 is shut off.

An opening/closing valve SV3 is disposed in a flow path connecting the compressor 82 and the second adsorption column 86, and another opening/closing valve SV4 is disposed in a flow path connecting the second adsorption column 86 and the discharge port 90. When the opening/closing valve SV3 is in an ON state, fluid can pass freely between the compressor 82 and the second adsorption column 86, and when the opening/closing valve SV3 is in an OFF state, flow of the fluid from the compressor 82 to the second adsorption column 86 is shut off. When the opening/closing valve SV4 is in an ON state, fluid can pass freely between the second adsorption column 86 and the discharge port 90, and when the opening/closing valve SV4 is in an OFF state, flow of the fluid from the second adsorption column 86 to the discharge port 90 is shut off.

A check valve 92, which allows fluid to flow only in a direction from the first adsorption column 84 to the tank 88, is disposed in a flow path connecting the first adsorption column 84 and the tank 88, and a check valve 94, which allows fluid to flow only in a direction from the second adsorption column 86 to the tank 88, is disposed in a flow path connecting the second adsorption column 86 and the tank 88.

In addition, the solenoid valve 10 according to the present embodiment is disposed in a flow path that is connected to downstream sides of the first adsorption column 84 and the second adsorption column 86. The solenoid valve 10 is arranged such that the first port 26 thereof is connected to the first adsorption column 84, and the second port 28 thereof is connected to the second adsorption column 86. For the sake of convenience, in FIG. 3, the solenoid valve 10 is shown in a simplified form by way of circuit elements thereof, and the first flow rate stabilizing orifice 34 and the second flow rate stabilizing orifice 36 are omitted from illustration.

When the oxygen concentrating device 80 is operated, the following processes from a first step to a sixth step are repeated. The first step includes an operation of returning from the sixth step to the first step, and since current is being supplied to the electromagnetic coil 56 of the solenoid valve portion 14 in the sixth step, in the first step, supply of current to the electromagnetic coil 56 of the solenoid valve portion 14 is suspended.
(First Step)

In a state in which the opening/closing valve SV1 and the opening/closing valve SV4 are both in an ON state, supply of current to the electromagnetic coil 56 of the solenoid valve portion 14 is suspended (time t1). The opening/closing valve SV2 and the opening/closing valve SV3 are both in an OFF state. At this time, since communication between the first passage 38 and the second passage 40 in the solenoid valve 10 is blocked, the first port 26 that is connected to the first adsorption column 84, and the second port 28 that is connected to the second adsorption column 86 are placed in communication only through the bypass flow path 42 in which the bypass orifice 44 is disposed.

Compressed air from the compressor 82 is delivered to the first adsorption column 84 through the opening/closing valve SV1, and by an action of the non-illustrated zeolite in the first adsorption column 84, nitrogen in the compressed air is adsorbed. Concentrated oxygen, which is produced by the first adsorption column 84, is delivered in large part to the tank 88, whereas a portion thereof, i.e., a part corresponding to a flow rate limited by the bypass orifice 44 of the solenoid valve 10, is delivered to the second adsorption column 86, and after being used for cleaning the zeolite of the second adsorption column 86, is discharged from the discharge port 90 via the opening/closing valve SV4. After the first step has elapsed beyond a predetermined time period, the zeolite of the first adsorption column 84 reaches a nitrogen adsorption limit.
(Second Step)

Thus, the electromagnetic coil 56 of the solenoid valve portion 14 is energized (time t2). Upon being energized, the movable iron core 62 is displaced axially, thereby causing the valve body 66 to separate away from the valve seat 68, and the fluid that flows in from the first port 26, which is of a higher pressure, flows toward the second port 28, which is of a lower pressure. The flow rate of the fluid that passes through the first flow rate stabilizing orifice 34 and the second flow rate stabilizing orifice 36 is significantly greater than the flow rate of the fluid that passes through the bypass orifice 44, and in the second step, concentrated oxygen is made to flow rapidly from the first adsorption column 84 to the second adsorption column 86.
(Third Step)

Thereafter, the opening/closing valve SV1 and the opening/closing valve SV4 are placed in an OFF state (time t3). Consequently, the pressure of the first adsorption column 84 and the pressure of the second adsorption column 86 are substantially equalized.
(Fourth Step)

In a state in which the opening/closing valve SV2 and the opening/closing valve SV3 are both in an ON state, supply of current to the electromagnetic coil 56 of the solenoid valve portion 14 is suspended (time t4). Upon doing so, since communication between the first passage 38 and the second passage 40 in the solenoid valve 10 is blocked, the first port 26 that is connected to the first adsorption column 84, and the second port 28 that is connected to the second adsorption column 86 are placed in communication only through the bypass flow path 42 in which the bypass orifice 44 is disposed.

Compressed air from the compressor 82 is delivered to the second adsorption column 86 through the opening/closing valve SV3, and by an action of the non-illustrated zeolite in the second adsorption column 86, nitrogen in the compressed air is adsorbed. Concentrated oxygen, which is produced by the second adsorption column 86, is delivered in large part to the tank 88, whereas a portion thereof, i.e., a part corresponding to a flow rate limited by the bypass orifice 44 of the solenoid valve 10, is delivered to the first adsorption column 84, and after being used for cleaning the zeolite of the first adsorption column 84, is discharged from the discharge port 90 via the opening/closing valve SV2. After a predetermined time period of the fourth step has elapsed, the zeolite of the second adsorption column 86 reaches a nitrogen adsorption limit.

(Fifth Step)

Thus, the electromagnetic coil 56 of the solenoid valve portion 14 is energized (time t5). Upon being energized, the movable iron core 62 is displaced axially, thereby causing the valve body 66 to separate away from the valve seat 68, and the fluid that flows in from the second port 28, which is of a higher pressure, flows toward the first port 26, which is of a lower pressure. The flow rate of the fluid that passes through the first flow rate stabilizing orifice 34 and the second flow rate stabilizing orifice 36 is significantly greater than the flow rate of the fluid that passes through the bypass orifice 44, and in the fifth step, concentrated oxygen is made to flow rapidly from the second adsorption column 86 to the first adsorption column 84.

(Sixth Step)

Thereafter, the opening/closing valve SV2 and the opening/closing valve SV3 are placed in an OFF state (time t6). Consequently, the pressure of the first adsorption column 84 and the pressure of the second adsorption column 86 are substantially equalized.

According to the solenoid valve 10 of the present embodiment, in the event that fluid flows from the first port 26 to the second port 28, or in the event that fluid flows from the second port 28 to the first port 26, even if the flow direction of the fluid in the vicinity of the valve body 66 is different, the flow rate is governed in particular by the flow rate stabilizing orifice that exists on the downstream side from among the first flow rate stabilizing orifice 34 and the second flow rate stabilizing orifice 36. For this reason, a structure can be provided in which a difference in flow rates does not occur, whether in the case that the fluid flows from the first port 26 to the second port 28, or in the case that the fluid flows from the second port 28 to the first port 26.

Further, since the solenoid valve 10 is constituted from the single solenoid valve portion 14 and the solenoid valve mounting portion 12 in which the first port 26 and the second port 28 are formed, a reduction in size of the solenoid valve portion 14 can be realized without the need for a manifold structure. Furthermore, there is no need for a specialized control circuit.

Furthermore, the first passage 38 that leads to the first flow rate stabilizing orifice 34, and the second passage 40 that leads to the second flow rate stabilizing orifice 36 are formed in the solenoid valve mounting portion 12, and the valve seat 68 on which the valve body 66 can be seated is formed in the circular-shaped open end of the second passage 40. In addition, since the open end of the first passage 38 is annularly shaped surrounding the circumference of the open end of the second passage 40, the structure for arranging the valve body 66 with respect to the flow path can be simplified.

Further still, the first flow rate stabilizing orifice 34 and the second flow rate stabilizing orifice 36 are constituted from passages defined by one surface of the first partition wall 30, which is disposed in the bore 22, and an inner wall surface of the bore 22. Together therewith, the bypass flow path 42 is disposed on an opposite side of the first partition wall 30 from the one surface. Therefore, the first flow rate stabilizing orifice 34, the second flow rate stabilizing orifice 36, and the bypass orifice 44 can be arranged compactly in the interior of the solenoid valve mounting portion 12 in which the first port 26 and the second port 28 are formed.

Further, the bypass orifice 44 is disposed in a substantially central position in the longitudinal direction of the bypass flow path 42, and the cross sectional area of the bypass flow path 42 is substantially constant from respective ends in the longitudinal direction to predetermined positions in the vicinity of the bypass orifice 44, whereas the cross sectional area gradually becomes smaller from the predetermined positions toward the bypass orifice 44. Therefore, in the bypass flow path 42 that includes the bypass orifice 44, the flow of the fluid can be made smoothly laminar.

Furthermore, since the solenoid valve mounting portion 12 including the first partition wall 30 and the second partition wall 32 is formed from a resin, it is unnecessary for the first flow rate stabilizing orifice 34, the second flow rate stabilizing orifice 36, and the bypass orifice 44 to be formed from separate components or to be formed by a cutting process, and thus the solenoid valve mounting portion 12 can be manufactured inexpensively at a low cost.

The solenoid valve according to the present invention is not limited to the above described embodiment, and various other structures may be adopted as a matter of course without deviating from the essence and gist of the present invention.

What is claimed is:

1. A solenoid valve arranged in a flow path in which a fluid flows in both directions, comprising:
    a solenoid valve mounting portion having a first port and a second port for the fluid flow;
    a single solenoid valve portion having a valve body and being provided between the first port and the second port in the fluid flow path;
    a first flow rate stabilizing orifice disposed between the first port and the valve body of the solenoid valve portion, the first flow rate stabilizing orifice being configured such that the fluid flow rate from the first port to the second port is controlled by the first flow rate stabilizing orifice;
    a second flow rate stabilizing orifice disposed between the second port and the valve body, the second flow rate stabilizing orifice being configured such that the fluid flow rate from the second port to the first port is controlled by the second flow rate stabilizing orifice;
    a bypass flow path that bypasses the first flow rate stabilizing orifice and the second flow rate stabilizing orifice; and
    a bypass orifice disposed in the bypass flow path,
    wherein the first flow rate stabilizing orifice and the second flow rate stabilizing orifice are symmetrically configured such that the fluid flow rate from the first port to the second port and the fluid flow rate from the second port to the first port, respectively controlled by the first flow rate stabilizing orifice and the second flow rate stabilizing orifice, are the same.

2. The solenoid valve according to claim 1, wherein:
    the first port and the second port are disposed on opposite ends of a bore that is formed in the solenoid valve mounting portion;
    the first flow rate stabilizing orifice and the second flow rate stabilizing orifice are constituted from passages defined by one surface of a partition wall disposed in the bore and an inner wall surface of the bore; and
    the bypass flow path is disposed on an opposite side of the partition wall from the one surface.

3. The solenoid valve according to claim 1, wherein:
    the bypass orifice is disposed in a substantially central position in a longitudinal direction of the bypass flow path; and
    a cross sectional area of the bypass flow path is substantially constant from respective ends in the longitudinal direction to predetermined positions in vicinity of the bypass orifice, and gradually becomes smaller from the predetermined positions toward the bypass orifice.

4. The solenoid valve according to claim 1, wherein the solenoid valve mounting portion is formed from a resin.

5. The solenoid valve according to claim 1, wherein the fluid is concentrated oxygen.

6. The solenoid valve according to claim 1, wherein the solenoid valve mounting portion further comprises:
   a first passage that leads to the first flow rate stabilizing orifice and a second passage that leads to the second flow rate stabilizing orifice; and
   a valve seat on which the valve body can be seated formed in one open end of one of the first passage and the second passage.

7. The solenoid valve according to claim 6, wherein the one open end is circular shaped, and another open end of another one of the first passage and the second passage is annularly shaped surrounding a circumference of the one open end.

* * * * *